| United States Patent [19] | [11] Patent Number: 4,875,602 |
| Chickering et al. | [45] Date of Patent: Oct. 24, 1989 |

[54] SELF-CONTAINED LIQUID DISPENSING DEVICE

[75] Inventors: Robert Chickering, Corona Del Mar, Calif.; William A. Barabino, North Reading, Mass.

[73] Assignee: Triad Direct Incorporated, Placentia, Calif.

[21] Appl. No.: 206,726

[22] Filed: Jun. 15, 1988

[51] Int. Cl.[4] ............................................. B65D 37/00
[52] U.S. Cl. ................................... 222/187; 222/212; 222/541; 401/138; 401/185; 401/156
[58] Field of Search ................... 222/214, 94, 96, 104, 222/106, 192, 211, 421, 541, 187, 212; 401/184, 186, 276, 273, 272, 283, 138, 156, 185

[56] References Cited

U.S. PATENT DOCUMENTS

| 1,409,544 | 3/1922 | Hallock | 222/104 |
| 1,431,860 | 10/1922 | Zurbrigg | 222/421 |
| 2,272,364 | 2/1942 | Connors | 222/421 X |
| 2,576,403 | 11/1951 | Kirschenbaum | 222/421 |
| 2,634,025 | 4/1953 | Hausner | 222/104 |
| 2,887,708 | 5/1959 | Kane | 401/184 X |
| 2,976,560 | 3/1961 | Turner | 401/186 |
| 3,035,299 | 5/1962 | Gordon et al. | 401/273 X |
| 3,118,573 | 1/1964 | Johnson | 222/212 |
| 4,124,316 | 11/1978 | O'Rourke | 401/186 X |
| 4,133,457 | 1/1979 | Klassen | 222/212 |
| 4,696,328 | 9/1987 | Rhodes, Jr. | 222/541 |
| 4,811,866 | 3/1989 | Golias | 222/189 |

Primary Examiner—Kevin P. Shaver
Assistant Examiner—Gregory L. Huson
Attorney, Agent, or Firm—Richard C. Litman

[57] ABSTRACT

A liquid dispensing apparatus includes a self-contained source of fluid normally isolated within a reservoir bulb which is deformable to initially rupture a membrane allowing the fluid to be forced in an axial direction through a shaft bore to saturate a tip-mounted swab. Alternatively, this membrane may be positioned intermediate two aligned sections of the shaft or associated structure and is ruptured upon partial axial collapse of the sections. Several embodiments are proposed and in some, the membrane not only provides the initial containment of the fluid but also serves as a fluid-tight seal between axially adjacent portions of the structure.

10 Claims, 1 Drawing Sheet

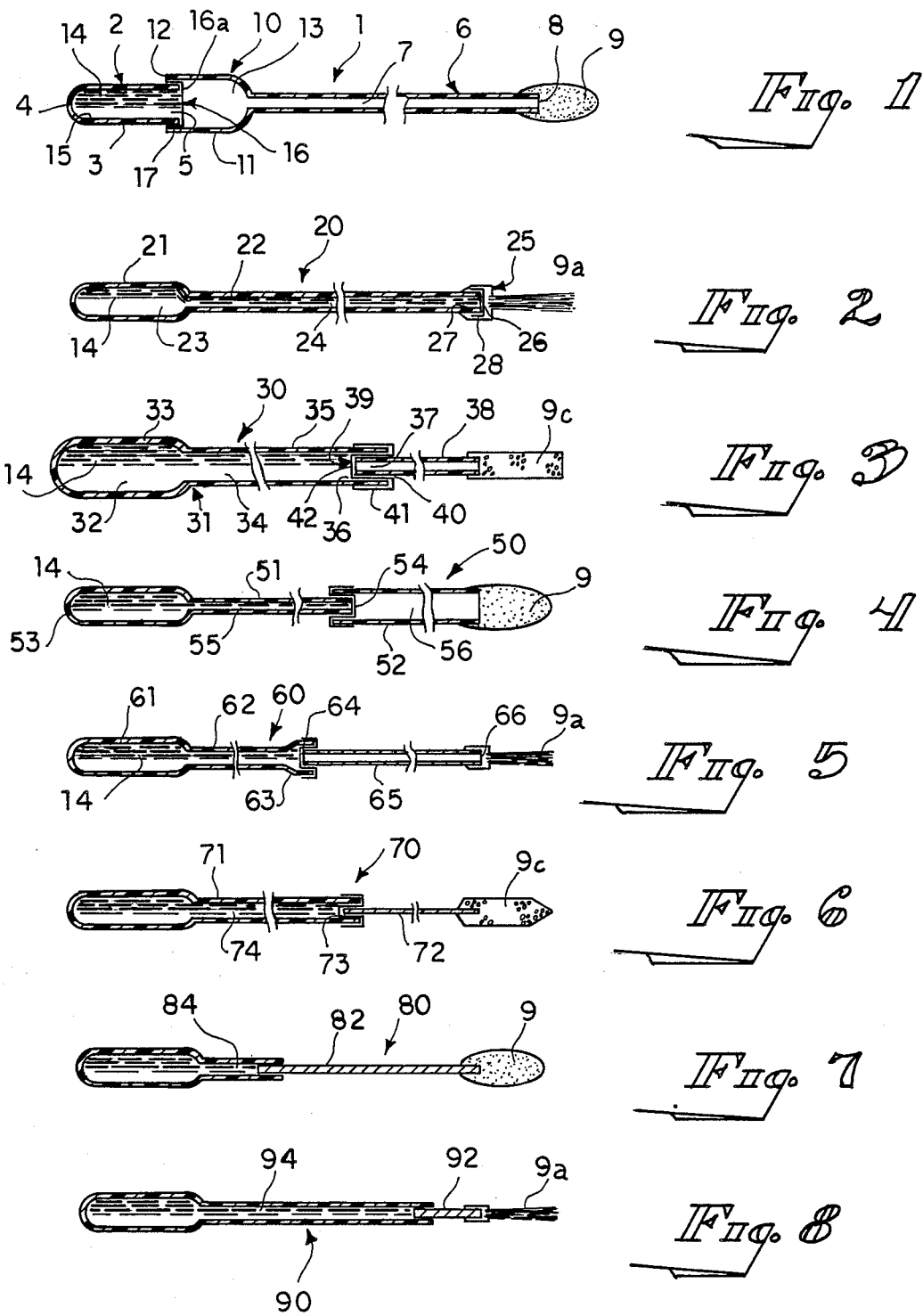

SELF-CONTAINED LIQUID DISPENSING DEVICE

BACKGROUND OF THE INVENTION

This invention relates generally, to liquid dispensing articles and more particularly, to improved liquid dispensing devices provided with an attached liquid supply.

Dispensing apparatus incorporating a liquid reservoir and having integral applicator means, are generally well known. Examples of prior devices will be found in U.S. Pat. Nos 3,495,917 to Truhan, issued Feb. 17, 1970 and 3,792,699 dated Feb. 19, 1974, issued to Tobin et al. These patents illustrate single-use swab-type applicators having a selfcontained liquid source and which are activated by the physical displacement of a portion thereof whereupon, liquid is forced through a pipette or tubular member, to a tip-mounted swab or applicator element. In each of these instances, a substantial number of components are required and there appears room for improvement in the degree of control available over the dispensing rate of the liquid to the swab.

SUMMARY OF THE INVENTION

By the present invention, an improved arrangement is provided wherein a self-contained liquid dispensing apparatus includes positive means isolating a liquid supply from a swab tip and which involves a minimum number of components, all of which are of simple construction and require but nominal effort to assemble. The resultant construction readily lends itself to mass production of low cost single-use, throw-away members which never-the-less offer a sanitary device for positively controlling the dispensing of any of numerous types of liquid products.

Various alternative embodiments of the instant invention are contemplated. In its broadest aspects, the invention comprises a liquid-containing, squeezeable or displaceable bulb, axially joined to a pipette and wherein a rupturable membrane or seal normally contains and isolates the liquid within the storage bulb. In use of the device, the bulb is squeezed and this pressure directs the liquid against the seal to cause its rupture and force the liquid through the bore of the pipette. An absorbent tip, such as a brush, cotton swab or sponge form, may be fixed directly upon the distal portion of the elongated pipette or alternatively, carried by the end of a extension member which is attached to the pipette end. In this latter instance, liquid urged from the end of the pipette encapsulates at least the external periphery of the extension member and travels to the end-mounted swab, brush or sponge form.

Accordingly, one of the objects of the present invention is to provide an improved self-contained liquid dispensing device including a fluid storage reservoir joined to a pipette terminating in a swab, brush or sponge form and which is provided with a rupturable membrane intermediate the reservoir and pipette.

Another object of the present invention is to provide an improved self-contained liquid dispensing device having a bulb adapted to initially contain a fluid and which is joined to a bored shaft by means of a partially rupturable member initially retaining the liquid within the bulb and also serving to sealingly join the bulb to the shaft.

A further object of the present invention is to provide an improved self-contained liquid dispensing device including a fluid-filled bulb communicating with a bored shaft in turn joined to a solid elongated member having a distal swab, brush or sponge form with a seal at the juncture of the shaft and member adapted to be ruptured by partial axial collapse of the member toward the shaft to allow fluid to migrate from the shaft bore along the member to the swab.

With these and other objects in view which will more readily appear as the nature of the invention is better understood, the invention consists in the novel construction, combination and arrangement of parts hereinafter more fully described, illustrated and claimed, with reference being made to the appended drawing.

BRIEF DESCRIPTION OF THE DRAWING

FIG. 1 is a longitudinal sectional view of a dispensing device according to the present invention and wherein, the fluid bulb is sealingly joined to an enlarged socket forming a part of a bored shaft terminating in a swab applicator;

FIG. 2 is a view similar to FIG. 1, of an alternate embodiment wherein the fluid bulb and bored shaft comprise an integral component terminating in a seal element within the confines of the tip-mounted brush applicator;

FIG. 3 is a view similar to FIG. 1, of an alternate embodiment wherein the bored shaft comprises two axially joined sections provided at their juncture with a combination rupturable membrane and seal element and wherein the tip-mounted applicator comprises0rises a sponge form;

FIG. 4 is a view similar to FIG. 3, of an alternate embodiment wherein the two different diameters of the shaft sections are reversed;

FIG. 5 is a view similar to FIG. 3, of an alternate embodiment wherein a modified adapter member is provided intermediate the bulb component and brush-equipped component;

FIG. 6 is a view similar to FIG. 3, of an alternate embodiment wherein the end-most bored shaft section is replaced by a solid element, allowing migration of liquid along its periphery; and FIGS. 7 and 8 are views similar to FIG. 6, illustrating variations of the bulb and solid elements.

Similar reference characters designate corresponding elements throughout the various figures of the drawing.

DESCRIPTION OF THE PREFERRED EMBODIMENT

Referring now to the drawing, the present invention will be understood to be directed to devices adapted to facilitate the dispensing of liquids, such as various medicaments, cosmetics, industrial fluids or the like. Although the concept set forth herein may be employed with devices of various sizes and fluid capacities, the disclosed features particularly lend themselves to throw-away devices of the one-shot type and which are readily mass produced. The dispenser 1 as shown in FIG. 1 of the drawing will be seen to comprise a bulb or reservoir 2 having a cylindrical outer wall 3 bounded on the one hand by an end wall 4 and on the other, by the illustrated open end 5.

The bulb 2 is adapted to be axially affixed to one end of a pipette comprising, in this embodiment, an elongated shaft 6 having a bore 7 therethrough. The forward, open end 8 of the shaft is surrounded by a suitable fluid applicator element such as the illustrated cotton swab 9. The opposite or rear of the shaft section is provided with an enlarged socket 10, likewise having a cylindrical wall 11 and terminating in a rear edge 12 whereby, an interior cavity 13 is formed therein.

The material selected for construction of the bulb and shaft components is preferably an appropriate synthetic resinous plastic. At least the bulb component must be deformable by finger pressure for reasons which will become apparent hereinafter. Alternately, the shaft component may be constructed of glass but in the interest of safety, manufacturing costs and assembly of the various components, a suitable deformable plastic is preferred also for the shaft member.

With a shaft 6 formed of plastic, the socket 10 is readily configured from a length of shaft stock, such as by controlled heating and the use of a stretch mold, as is well known in the art. The diameter of the socket wall 11 is formed to insure a close sliding fit of its rear edge 12 about the outer wall 3 of the bulb 2. Prior to this last mentioned assembly, the intended liquid 14 is placed within the cavity 15 of the bulb and a closure-seal member 16 applied over the bulb open end 5. The member 16 includes a central, transverse, membrane portion 16a spanning the bulb open end 5 to encapsulate or retain the liquid 14 as shown in FIG. 1, and a peripheral, flange or seal portion 17 overlying the forward portion of the bulb outer wall 3. In this manner the flange or seal portion 17 is sandwiched between the two cylindrical outer walls 3 and 11 and serves the dual purpose of fixedly joining the bulb to the shaft as well as provides a fluid-tight seal therebetween.

In operation of the above described dispensing device 1, the user places the outer wall 3 of the bulb 2 between two fingers and applies a squeezing pressure. The subsequent inward deformation of the resilient body of the bulb translates as a greater than atmospheric pressure upon the liquid 14 filling the cavity 15 and as this pressure is increased, the bursting strength of the membrane portion 16a will be exceeded and the membrane will be ruptured. Continued deformation of the bulb wall 3 will be understood to cause the liquid 14 to be directed through the socket cavity 13 and the shaft bore 7 until it reaches the shaft open end 8. At this point, the absorbency of the cotton tip or swab 9 causes the tip to become moistened, or even saturated, depending upon the duration and amount of deformation of the bulb.

In the embodiment shown in FIG. 2 of the drawing, the dispenser 20 includes an integral bulb 21 and shaft 22. With this arrangement, the desired liquid 14 initially fills not only the bulb cavity 23 but also the bore 24 of the adjacent shaft 22. During manufacture, the filled liquid is retained by means of the closure-seal member 25 which is similar to the member 16 of FIG. 1. The central, membrane portion 26 initially encloses the open end 27 of the shaft 22 while the peripheral flange portion 28 is folded back upon the shaft end and suitably adhered thereto such as by heat sealing, or an adhesive. As in the embodiment of FIG. 1, the closure-seal 25 insures leak-proof retention of the liquid 14 within the bulb 21 and shaft 22 until the user wishes to dispense the liquid whereupon, a squeezing pressure upon the bulb 21 is transmitted to the liquid within the shaft bore 24 to cause rupture of the membrane portion 26 and the subsequent moistening of the tip applicator, such as the illustrated brush 9a. Quite obviously the bursting strength and/or density of the swab material in the area of the membrane will be selected to permit the above described rupturing of the membrane within the confines of the brush while still insuring fluid-tight containment of the liquid prior to its use.

Various tip-mounted applicators are shown in the plurality of embodiments illustrated and described herein and it will be understood that any one such applicator may be mounted on the tip of any version of the dispensing devices according to the present invention. The brush 9a may comprise natural or synthetic fibers.

FIGS. 3 and 4 illustrate alternate embodiments 30 and 50 of dispensers allowing of variation of the pressure transference from a squeezed bulb and the oppositely disposed tip applicator. In both of these instances, a pair of axially aligned, concentrically joined, shafts convey the displaced fluid 14 from the bulb to the tip 9 or 9b. Each version employs a unitary bulb and bored bulb shaft and which is affixed to a bored tip shaft having a different diameter than the bulb shaft.

The dispenser 30 of FIG. 3 includes a bulb-shaft unit 31 wherein the cavity 32 of the bulb 33 communicates with the bore 34 of the integral bulb shaft 35, the latter of which terminates in an open end 36. The rear, open end 37 of a tip shaft 38 is nested within the bore 34 of the larger diameter bulb shaft 35 and fixedly joined thereto by means of the closure-seal member 39. This member 39 will be understood to provide an enhanced fluid-tight attachment between the two shafts of differing diameters, in view of the labyrinth arrangement offered by the inner flange 40 and outer flange 41 respectively, joining the two concentric portions of the shafts together and secured about the external periphery of the bulb shaft end 36. The central, rupturable portion 42 of the membrane member 39 functions in the manner as previously described herein. Note that the applicator 9b depicts a typical sponge form.

The construction of the dispenser 50 shown in FIG. 4 is similar to that as related with respect to the dispenser of FIG. 3 with the exception that the relative diameters of the two shafts are reversed. More specifically, it will be noted that the bulb shaft 51 is of a lesser diameter than that of the tip shaft 52. Normally, this latter construction will result in greater efficiency of pressure transference as liquid 14 is forced from the bulb 53 and subsequently urged to rupture the larger area of the membrane portion 54 that spans the larger diameter of the tip shaft bore 56. Although the pressure as applied by the user will remain substantially constant, it will be understood that the force required to rupture the sealing membrane 54 will equal the applied pressure times the membrane area.

The arrangement of the embodiment shown in FIG. 5 may be considered a combination of features advanced by the above described versions of FIGS. 3 and 4. The dispenser 60 includes a bulb 61 integral with a bulb shaft 62 which will be seen to have a relative large diameter but which is joined to an enlarged conical section 63 terminating in a longitudinally extending end flange 64. In this manner, the still larger diameter of the conical section is capable of accommodating a bored tip shaft 65 which quite obviously may be of greater diameter than the tip shaft 38 as shown in the dispenser 30 of FIG. 3. In this manner, the increased membrane area increases the available rupture force.

The dispensers 70, 80, 90 shown in FIGS. 6, 7 and 8 respectively, introduce the concept of substituting a non-bored tip shaft in the case of the component supporting the applicator tip 9c, 9 or 9a and wherein, activation of the liquid dispensing is accomplished by the axial, counter-displacement of the tip shaft relative the bulb shaft. In each instance, an integral bulb is depicted with a bored bulb shaft of a particular length and which is combined with a relatively solid tip shaft, which also may be of varied length. With this construction, axial displacement of the the tip shaft thus fractures the fluid seal between the two shaft members to initiate the passage of the liquid from the bulb shaft bore 74,84 or 94 to the rear end of the solid tip shaft 72,82 or 92. The liquid then migrates radially about the tip shaft and traverses the periphery thereof by normal wetting action, to the end-most cotton or other applicator tip. Subsequent squeezing of the bulb augments this liquid flow.

The actual construction of the tip shaft may vary. For example, porous or paper material may be used in its manufacture and in some instances, there will be a degree of migration internally thereof, as well as radially and along its periphery.

The dispenser 70 of FIG. 6 shows a bulb shaft 71 and tip shaft 72, both of intermediate length and sealed and affixed to one another by means of the closure-seal 73. This latter connection will be seen to be similar to that as shown in the embodiment of FIG. 3, although the operation thereof is dissimilar as described above. An alternate tip applicator comprising a knife edge sponge form 9c is shown with this dispensing device.

The remaining dispensers 80 and 90 illustrated in FIGS. 7 and 8 follow the same teaching as advanced by the embodiment of FIG. 6 and reflect variation of the bulb shaft and tip shaft lengths to achieve alternate fluid transference for a given pressure application upon the associated bulb. Although separate closure-seal members are not shown in these latter figures, it will be appreciated that the same member 73 of FIG. 6 may be employed with these dispensers. Depending upon the material of the solid tip shafts, the specific liquid employed and the clearance between the two shafts, adequate fluid-tight sealing may be provided without a separate member. In this respect, a normally fluid-tight seal may be provided by an appropriate pressure fit between the two members and which allows the abovementioned fluid migration upon the axial collapse of the two members and subsequent squeezing of the associated bulb. In any case the liquid will be understood to migrate from the bored bulb shaft and flow along the outside of the tip shaft to the endmost applicator tip element.

We claim:

1. A liquid dispensing device comprising;
    a squeezable elongated cylindrical bulb adapted to be compressed between two fingers of a user and provided with a cavity adapted to contain a liquid desired to be dispensed,
    said bulb having an axial extent defining a length substantially greater than the diameter of said bulb,
    an elongated bulb shaft having a forward end and an axial bore therethrough communicating with said bulb cavity,
    said bulb shaft defining an axial extent having a length no less than that of said bulb axial extent with said bulb shaft bore defining a diameter substantially less than that of said bulb cavity,
    an elongated tip shaft having rearward and forward ends and provided with a central bore,
    said bulb shaft and tip shaft each having a substantially constant configuration throughout their respective lengths,
    an applicator tip supported upon said tip shaft forward end,
    said tip comprising a disparate form adapted to receive and retain liquid for direct transfer to another member,
    said bulb shaft and tip shaft of differing diameters and concentrically joined to one another,
    normally fluid-tight means intermediate said bulb cavity and said tip shaft rearward end, said fluid-tight means including a rupturable closure-seal member initially transversely spanning said bulb shaft bore and isolating liquid within said bulb from said tip shaft bore, said closure-seal member including an integral flange sealingly joining an end of said bulb shaft to said tip shaft rearward end whereby,
    upon squeezing of said bulb by a user's fingers, pressure is applied to liquid within said bulb cavity, causing a rupture of said closure-seal member and advancement of the liquid within said bulb cavity through said bulb shaft bore and said tip shaft bore and thence to said applicator tip.

2. A liquid dispensing device according to claim 1 wherein,
    said tip shaft rearward end includes an enlarged socket.

3. A liquid dispensing device according to claim 1 wherein,
    said bulb and bulb shaft are integral.

4. A liquid dispensing device according to claim 1 wherein,
    said bulb and bulb shaft are of plastics.

5. A liquid dispensing device according to claim 1 wherein,
    said applicator tip comprises a cotton form.

6. A liquid dispensing device according to claim 1 wherein,
    said applicator tip comprises a fiber brush.

7. A liquid dispensing device according to claim 1 wherein,
    said applicator tip comprises a sponge form.

8. A liquid dispensing device according to claim 1 wherein,
    said tip shaft diameter is greater than said bulb shaft diameter.

9. A liquid dispensing device according to claim 1 wherein,
    said tip shaft diameter is less than said bulb shaft diameter.

10. A liquid dispensing device according to claim 1 wherein,
    said fluid-tight means comprises a plastics member overlying said bulb shaft forward end.

* * * * *